(12) United States Patent
Seki et al.

(10) Patent No.: US 9,632,151 B2
(45) Date of Patent: Apr. 25, 2017

(54) MAGNETIC RESONANCE MEASURING EQUIPMENT

(75) Inventors: Yusuke Seki, Tokyo (JP); Takashi Azuma, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 667 days.

(21) Appl. No.: 14/125,604

(22) PCT Filed: Jun. 25, 2012

(86) PCT No.: PCT/JP2012/066104
§ 371 (c)(1),
(2), (4) Date: Feb. 21, 2014

(87) PCT Pub. No.: WO2013/002159
PCT Pub. Date: Jan. 3, 2013

(65) Prior Publication Data
US 2014/0167761 A1 Jun. 19, 2014

(30) Foreign Application Priority Data
Jun. 28, 2011 (JP) ................................. 2011-142448

(51) Int. Cl.
*G01R 33/34* (2006.01)
*G01R 33/48* (2006.01)
(Continued)

(52) U.S. Cl.
CPC .......... *G01R 33/34* (2013.01); *G01N 24/08* (2013.01); *G01R 33/326* (2013.01);
(Continued)

(58) Field of Classification Search
CPC ...... G01N 24/08; G01R 33/34; G01R 33/326; G01R 33/4808; G01R 33/4814; G01R 33/56
See application file for complete search history.

(56) References Cited

U.S. PATENT DOCUMENTS

| 4,987,368 A | 1/1991 | Vinegar |
| 2009/0072828 A1* | 3/2009 | Penanen ............ G01R 33/0354 |
| | | 324/318 |

FOREIGN PATENT DOCUMENTS

| JP | 01-155291 A | 6/1989 |
| JP | 2010-447417 A | 10/2010 |

OTHER PUBLICATIONS

Machine Translation of JP 2010-227417 A obtained on Aug. 26, 2016.*

(Continued)

*Primary Examiner* — Gregory H Curran
(74) *Attorney, Agent, or Firm* — Mattingly & Malur, PC (57) ABSTRACT

A magnetic resonance measuring equipment capable of detecting a nuclear magnetic resonance signal with a higher sensitivity and a higher resolution in comparison with related magnetic resonance measuring equipment. The magnetic resonance measuring equipment modulates a nuclear magnetic resonance signal by applying a vibration (sonic wave) of a known frequency, which is higher than the frequency of the nuclear magnetic resonance signal, to an examination object, and detects the modulated signal by performing lock-in detection, which makes it possible that the magnetic resonance measuring equipment detects the nuclear magnetic resonance signal with a high sensitivity. In addition, after irradiating a local area of the object with an ultrasonic wave, and modulating the nuclear magnetic resonance signal derived from the irradiated local area, the magnetic resonance measuring equipment can detect the nuclear magnetic resonance signal with a high resolution.

9 Claims, 11 Drawing Sheets

(51) Int. Cl.
   *G01R 33/56*   (2006.01)
   *G01N 24/08*   (2006.01)
   *G01R 33/32*   (2006.01)
(52) U.S. Cl.
   CPC ..... *G01R 33/4808* (2013.01); *G01R 33/4814* (2013.01); *G01R 33/56* (2013.01)

(56) References Cited

OTHER PUBLICATIONS

Haacke et al., "Magnetic Resonance Imaging: Physical Principles and Sequence Design", Wiley—Liss, 1999, pp. 1-15.
Edited by Clarke et al., "The SQUID Handbook, vol. I: Applications of SQUIDs and SQUID Systems", Wiley-VCH Verlag GmbH & Co. KGaA, 2004, pp. 1-28.
Clarke et al., "Squid-Detected Magnetic Resonance Imaging in Microtesla Fields", Annual Review of Biomedical Engineering 2007, vol. 9, pp. 389-413.
Liao et al., Longitudinal Relaxation Time Detection Using a High-Tc Superconductive Quantum Interference Device m, Journal of Applied Physics, 2007, vol. 102, pp. 33914-1 to 33914-4.

\* cited by examiner

FIG.11 yz CROSS-SECTION OF 301

MAGNETIC RESONANCE MEASURING EQUIPMENT

TECHNICAL FIELD

The present invention relates to a technology for measuring a nuclear magnetic resonance signal of an object with a high sensitivity with the use of an ultrasonic wave.

BACKGROUND ART

NMR (nuclear magnetic resonance) or MRI (magnetic resonance imaging) is a method for measuring the structure and property of an examination object with the use of an atomic nucleus as a probe, and has been widely used in the medical field and inspection field (Nonpatent Literature 1). The frequency of the nuclear magnetic resonance signal is proportional to the intensity of a static magnetic field, and the proportionality coefficient is a constant peculiar to an atomic nucleus, and is referred to as the gyromagnetic ratio of the nucleus. For example, the gyromagnetic ratio of a proton $^1H$ is 42.58 MHz/T (tesla). Generally, as the intensity of the static magnetic field becomes stronger, the sensitivity and the resolution of the measurement become more improved; therefore, the intensity of the static magnetic field currently used for the NMR/MRI is equal to 1 T or larger. Therefore a static magnetic field coil used for the NMR/MRI is comprised of superconducting wires.

Generally, an induction coil is used for detecting a nuclear magnetic resonance signal. The signal intensity obtained by the induction coil scheme is proportional to the product of the magnetic moment $M_o$ and the resonant angular frequency $\omega$ of a sample. $M_o$ and $\omega$ are respectively proportional to the intensity of a static magnetic field $B_o$, therefore the signal intensity is proportional to the square value of $B_o$. Therefore, if the intensity of the static magnetic field is small, the signal intensity becomes extremely small.

On the other hand, a measurement for measuring NMR/MRI in the region of an intensity of static magnetic field 10 µT to 100 µT, which is of the geomagnetic intensity level, that is, a measurement for measuring an ultralow magnetic field NMR/MRI has been widely attracting attention in recent years. The frequency of the nuclear magnetic resonance signal of a proton in the ultralow magnetic field NMR/MRI is about 1 kHz to 10 kHz, and this frequency is five to six digits lower than a frequency that is used in an ordinary magnetic field NMR/MRI. Therefore, the measurement in the ultralow magnetic field NMR/MRI is characterized in that, in order to obtain a high signal intensity, pre-polarization is performed on a nuclear spin of a measurement object with the use of a polarized magnetic field of about 10 mT to 100 mT, and a SQUID (superconducting quantum interference device: Nonpatent Literature 2), which is a high-sensitive magnetic sensor, is used instead of the induction coil (Nonpatent Literature 3).

Because a static magnetic field coil and a gradient magnetic field coil used in the ultralow magnetic field NMR/MRI are comprised of room-temperature cupper wire coils, these coils can be drastically downsized, can be made low cost, and can be improved in their safety aspect in comparison with a superconducting magnet. In addition, because the signal frequency decreases to the order of several kHz, the NMR/MRI can be performed in the presence of a metal body.

CITATION LIST

Nonpatent Literatures

Nonpatent Literature 1: "Magnetic Resonance Imaging: Physical Principles and Sequence Design", E. M. Haacke, R. W. Brown, M. R. Thompson, R. Venkatesan (Wiley-Liss), 1-15 (1999).

Nonpatent Literature 2: "The SQUID Handbook, vol. I: Applications of SQUIDs and SQUID Systems", edited by J. Clarke and A. I. Braginski (Wiley-VCH Verlag GmbH & Co. KGaA), 1-28 (2004).

Nonpatent Literature 3: J. Clarke, M. Hatridge, and M. Moβle, "SQUID-Detected Magnetic Resonance Imaging in Microtesla Fields", Annual Review of Biomedical Engineering 9, 389-413 (2007).

SUMMARY OF INVENTION

Technical Problem

In the measurement in the low magnetic field NMR/MRI, the frequency of the nuclear magnetic resonance signal is about several kHz, and this frequency is about five digits smaller than the frequency of a nuclear magnetic resonance signal used in the measurement in a related magnetic field NMR/MRI, therefore there is a problem in that the signal intensity used in the induction coil scheme is small. Currently, a SQUID magnetic flux meter is used for detecting the signal in the measurement in order to detect the signal with a high sensitivity. On the other hand, in comparison with the related method adopted in the measurement in the high magnetic field NMR/MRI, the method that uses the SQUID magnetic flux meter has some problems in that the sensitivity and the resolution are inferior and liquid helium is needed to cool the SQUID, so that the size of the detection unit becomes large and the cost of the detection unit is driven up.

Solution to Problem

An example of the present invention that solves the above problems is a magnetic resonance measuring equipment that includes: a static magnetic field coil for generating a static magnetic field; a vibrator for applying a vibration, whose frequency is higher than the frequency of a nuclear magnetic resonance signal generated from an examination object, to the examination object; and a probe for detecting the nuclear magnetic resonance signal generated from the examination object. In addition, this magnetic resonance measuring equipment is configured so that the nuclear magnetic resonance signal is modulated by the vibrator, then the modulated nuclear magnetic resonance signal is detected.

Advantageous Effects of Invention

The present invention can provide a magnetic resonance measuring equipment that can detect a nuclear magnetic resonance signal with a higher sensitivity and a higher resolution in comparison with related magnetic resonance measuring equipment.

DESCRIPTION OF EMBODIMENTS

Hereinafter, the examples of examinations of measurement objects according to the embodiments of the present invention will be explained in detail. The measurement objects (also referred to as examination objects) include biological samples, liquid samples, and solid samples.

Figure 1:
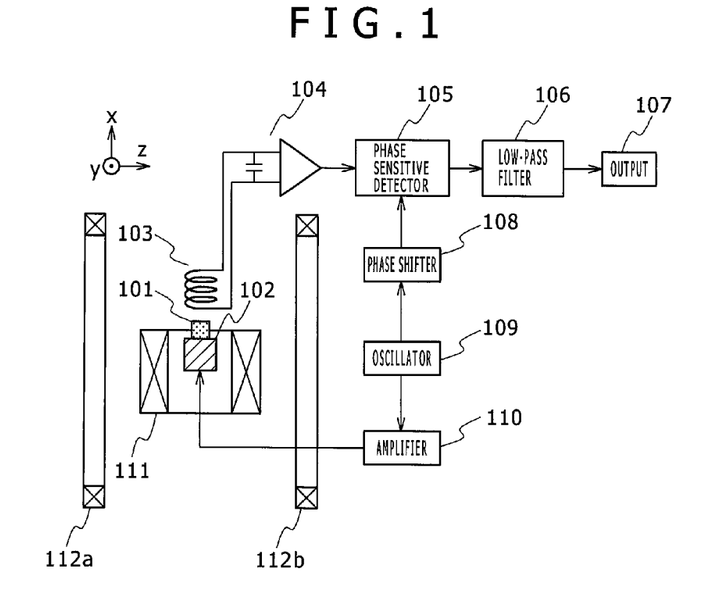
FIG. 1 is a schematic diagram showing a magnetic resonance measuring equipment according to the present embodiment.

FIG. 1 is a schematic diagram showing a magnetic resonance measuring equipment according to the present embodiment. A combination of static magnetic field coils 112a and 112b is a Helmholtz coil that includes two equivalent coils disposed opposite to each other. A uniform magnetic field whose direction is the z-direction is generated in the vicinity of an examination object 101 by these static magnetic field coils 112a and 112b. The intensity of this static magnetic field $B_o$ is approximately between 1 µT and 100 µT.

A polarization coil 111 is a solenoid coil, and generates an x-direction static magnetic field (polarized magnetic field). The intensity of the polarized magnetic field $B_p$ is approximately between several mT and several hundred mT. It is necessary that the direction of the polarized magnetic field should be perpendicular to the direction of the static magnetic field, so it is also all right if the direction of the polarized magnetic field is the y-direction. In addition, if the polarization coil is a Helmholtz coil that includes two solenoid coils disposed opposite to each other so that the examination object is located between the two solenoid coils, a more uniform and stronger polarized magnetic field $B_p$ can be generated.

The nuclear spin M of an atom included in the examination object 101 is magnetized in the x-direction by the polarized magnetic field $B_p$ generated by the polarization coil 111. When the application of the polarized magnetic field $B_p$ to the examination object 101 is stopped after the polarized magnetic field $B_p$ is applied for about a longitudinal relaxation time, the nuclear spin M is relaxingly magnetized in the direction of the static magnetic field $B_o$.

At this time, a nuclear magnetic resonance signal of the frequency $f_o$ proportional to the static magnetic field $B_o$ is generated from the examination object 101, and decays with a transverse relaxation time T2. This nuclear magnetic resonance signal is the most fundamental nuclear magnetic resonance signal referred to as a free induction decay (FID) signal.

For example, if the intensity of the static magnetic field is 50 µT, the frequency of a nuclear magnetic resonance signal derived from a proton is 2.1 kHz. In addition, irradiating signals called RF pulses with the use of an RF (radio frequency) coil (not shown in FIG. 1) makes it possible to handle the nuclear spins.

In this case, if a vibrator 102 applies a vibration (sonic wave) of a vibration frequency F higher than the signal frequency $f_o$ to the examination object 101, the examination object 101 vibrates at the vibration frequency F. It is desirable that the vibration frequency F should be 10 times the signal frequency $f_o$ or higher.

An actuator and a speaker that utilize piezoelectric effect or electrostriction effect, a MEMS switch that utilizes electrostatic force, and an eccentric motor that converts its rotation movement into a vibration can be used as the vibrator 102.

As described above, the lower limit of the vibration frequency F has been discussed, the upper limit of the vibration frequency F will be discussed hereinafter. There are two apprehensions below if the vibration frequency F is too high. First, there is a possibility that, because the vibration of the frequency F decays while propagating inside an examination object, the vibration can be effectively applied only to part of the examination object near to the vibrator. Secondly, even if the vibration can be effectively applied to the examination object, there is a possibility that the frequency of electromagnetic wave generated in the deep portion of the examination object is too high, and decays too much to reach a coil.

First, the decay of an ultrasonic wave will be discussed. It is known that a biomedical tissue has a ultrasonic wave decay rate of about 0.6 dB/MHz/cm. Because it is desirable that the sensitivity of the magnetic resonance measuring equipment should be constant across the imaging view field, it is necessary that the ratio of the amplitude of the ultrasonic wave at the position farthest from the vibrator (the signal of the ultrasonic wave is the weakest) to the amplitude of the ultrasonic wave at the position nearest to the vibrator (the signal of the ultrasonic wave is the strongest) should be 1/10 or larger. As a result of the above discussion, the upper limit of the frequency F turns out to be 330 MHz if the size of the examination object is 1 mm, 33 MHz if 1 cm, and 3.3 MHz if 10 cm. On the other hand, in the case of an examination object that has a small decay ratio such as water, the upper limit of the frequency F is determined taking the electromagnetic wave absorption factor of the examination object into consideration.

Next, the decay of the nuclear magnetic resonance signal will be discussed. It is necessary that the ratio of the amplitude of the nuclear magnetic resonance signal at the position farthest from the vibrator (the signal is the weakest) to the amplitude of the nuclear magnetic resonance signal at the position nearest to the vibrator (the signal is the strongest) should be 1/10 or larger. It is known that the decay ratio of an electromagnetic wave, which is the nuclear magnetic resonance signal, is proportional to $1/\sqrt{f}$, where f is the frequency of the electromagnetic wave. In addition, the electromagnetic wave of 1 GHz decays to one tenth per about 7 cm in a living organism. Therefore, the upper limit of the frequency of the nuclear magnetic resonance signal is 1 THz (terahertz) if the size of the examination object is 1 mm, 50 GHz if 1 cm, and 500 MHz if 10 cm.

A piezoelectric substance, a speaker, and a motor can be used as the vibrator 102. An induced electromotive force proportional to the derivative of the magnetic flux across a detection coil 103 with respect to time is generated between the terminals of the detection coil 103 that is an induction coil, where the magnetic flux across the detection coil 103 is induced by the nuclear magnetic resonance signal generated from the examination object 101.

Because the magnetic flux across the detection coil 103 is modulated by the vibration frequency F, the induced electromotive force induced at the detection coil 103 is also modulated by the vibration frequency F. In addition, because the intensity of the induced electromotive force induced at the detection coil 103 is proportional to the vibration frequency F, the intensity of the induced electromotive force induced at the detection coil 103 becomes larger as the vibration frequency F becomes higher, and also the intensity of the induced electromotive force induced at the detection coil 103 becomes larger as the amplitude of the vibration of the examination object 101 becomes larger.

In addition, by modulating the voltage signal, it becomes possible that the spectra of the signal components are separated from the main components of the spectra of the noise components, and that the signal is detected with a high signal-to-noise ratio by a phase sensitive detector (PSD) 105. In other words, a lock-in detection becomes available.

The nuclear magnetic resonance signal modulated by the frequency F is detected by the detection coil 103, amplified by a tuning amplifier 104, and input into the phase sensitive detector 105. In this case, the phase sensitive detector 105 outputs the product of the nuclear magnetic resonance signal modulated by the frequency F and a reference signal of the frequency F, and after the product passes through a low-pass filter 106, only the original nuclear magnetic resonance signal can be detected with a high S/N ratio.

Figure 2:
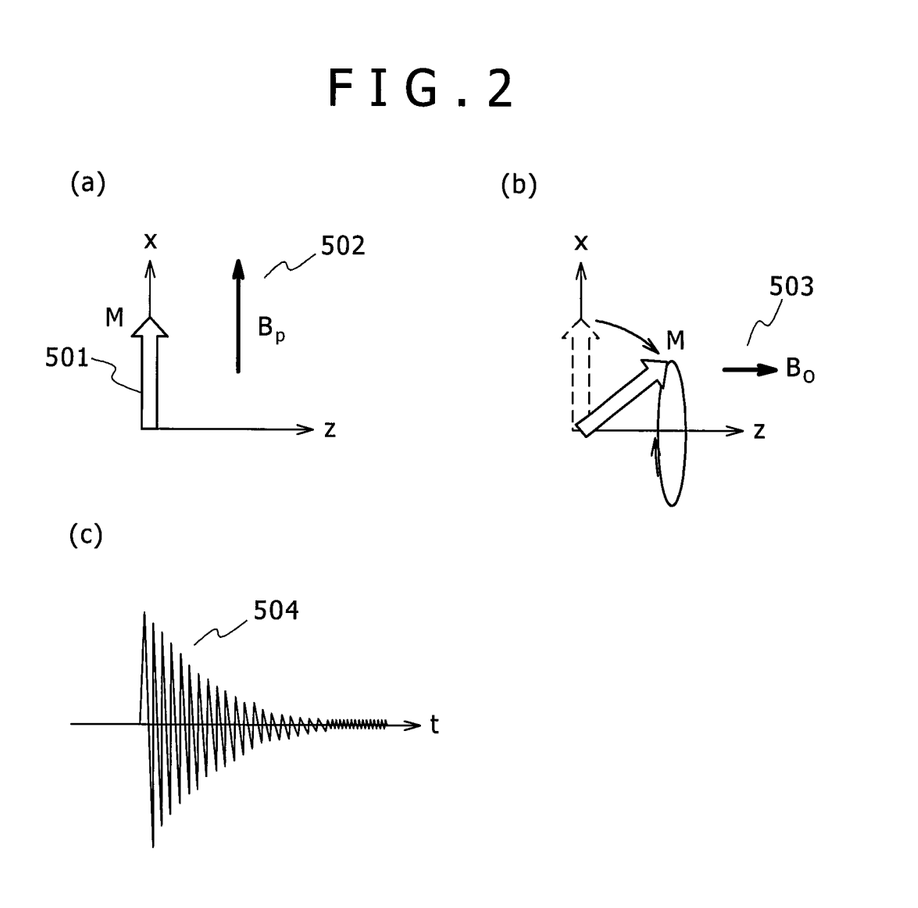
FIG. 2 is a schematic diagram showing a measurement principle of the magnetic resonance measuring equipment according to the present embodiment.

FIG. 2 is a schematic diagram showing a measurement principle of the magnetic resonance measuring equipment according to the present embodiment. FIG. 2(a) is a diagram showing a nuclear spin M 501 of an atom included in the examination object 101 that is magnetized in the x-direction by the polarized magnetic field $B_p$ 502 generated by the polarization coil 111.

FIG. 2(b) is a diagram showing a condition in which, when the application of the polarized magnetic field $B_p$ 502 to the examination object 101 is stopped after the polarized magnetic field $B_p$ 502 is applied for about a longitudinal relaxation time, the nuclear spin M 501 is relaxingly magnetized in the direction of the static magnetic field $B_o$ 503.

FIG. 2(c) is a diagram showing a nuclear magnetic resonance signal 504 of the frequency $f_o$ proportional to the static magnetic field $B_o$ 503 generated from the examination object 101. This nuclear magnetic resonance signal is the most fundamental nuclear magnetic resonance signal referred to as a free induction decay (FID) signal, and decays with a transverse relaxation time T2.

Because the magnetic flux across the detection coil 103 is modulated by the vibration frequency F, the induced electromotive force induced at the detection coil 103 is also modulated by the vibration frequency F. In addition, because the intensity of the induced electromotive force induced at the detection coil 103 is proportional to the vibration frequency F, the intensity of the induced electromotive force becomes larger as the vibration frequency F becomes higher, and also the intensity of the induced electromotive force becomes larger as the amplitude of the vibration of the examination object 101 becomes larger.

In addition, by modulating the voltage signal, it becomes possible to separate the spectra of the signal components from the main components of the spectra of the noise components, and the signal is detected with a high signal-to-noise ratio by a phase sensitive detector (PSD) 105. In other words, a lock-in detection becomes available.

The nuclear magnetic resonance signal modulated by the frequency F is detected by the detection coil 103, amplified by the tuning amplifier 104, and input into the phase sensitive detector 105. In this case, the phase sensitive detector 105 outputs the product of the nuclear magnetic resonance signal modulated by the frequency F and the reference signal of the frequency F, and after the product passes through the low-pass filter 106, only the original nuclear magnetic resonance signal can be detected with a high S/N ratio.

Figure 3:
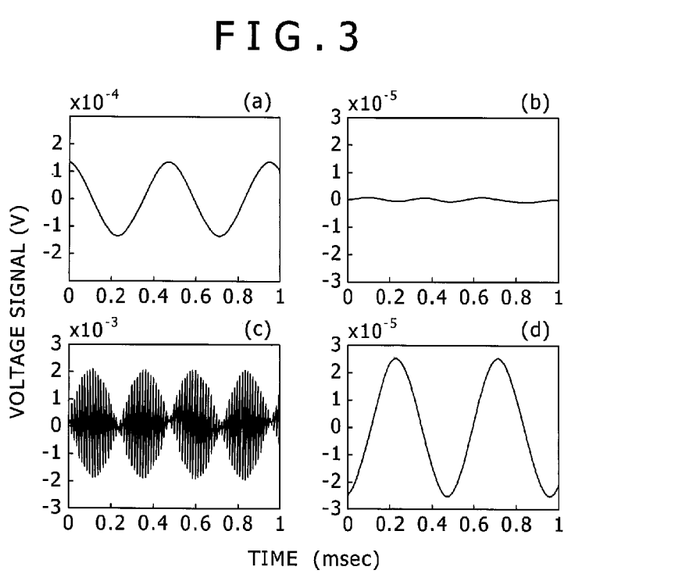
FIG. 3 is a schematic diagram showing examples of measurement signals of the magnetic resonance measuring equipment according to the present embodiment.

FIG. 3 is a schematic diagram showing examples of measurement signals of the magnetic resonance measuring equipment according to the present embodiment. FIG. 3(a) is a diagram showing a voltage signal obtained when the nuclear magnetic resonance signal of a proton in the static magnetic field with its intensity 50 µT is detected by an induction coil in the case of the examination object 101 being in resting state. As described above, the frequency of the voltage signal is 2.1 kHz. In this case, because the induction coil is used, the voltage signal is proportional to the derivative of the nuclear magnetic resonance signal generated from the examination object, that is, a magnetic signal B(t) with respect to time. On the other hand, FIG. 3(c) is a diagram showing a voltage signal obtained when the examination object 101 is vibrated with the vibration frequency 100 kHz. In addition, FIG. 3(d) is a diagram showing a waveform obtained by performing lock-in detection on the signal shown in FIG. 3(c) using a reference signal of the frequency F. On the other hand, FIG. 3(b) is a diagram showing a signal obtained by performing lock-in detection on the unmodulated signal shown in FIG. 3(a) using a reference signal of the frequency F in a similar way as above. It is obvious that the amplitude of the signal is almost vanished. Judging from the above, it is understood that only the nuclear magnetic resonance signal that is derived from the sample and modulated by the vibration frequency F can be measured by this measurement method which employs the modulation using the vibration and the lock-in detection.

Figure 4:
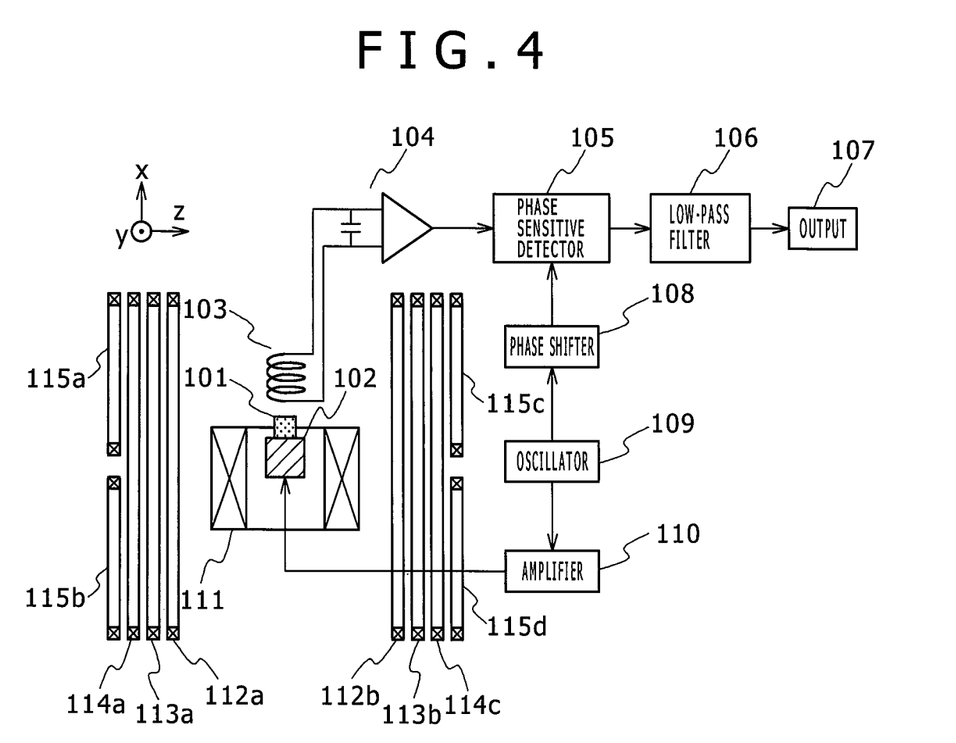
FIG. 4 is a schematic diagram showing a magnetic resonance measuring equipment according to the present embodiment.

FIG. 4 is a schematic diagram showing a magnetic resonance measuring equipment according to the present embodiment. The configuration of the magnetic resonance measuring equipment shown in FIG. 4 is a configuration of the magnetic resonance measuring equipment shown in FIG. 1 to which gradient magnetic field coils are added, with the result that the magnetic resonance measuring equipment shown in FIG. 4 becomes capable of imaging.

Gradient magnetic coils 113a and 113b are disposed opposite to each other, and directions of currents that flow through the gradient magnetic coils 113a and 113b are opposite to each other, which generates a gradient magnetic field $\partial Bz/\partial z$ in the vicinity of the examination object 101. A combination of the gradient magnetic coils 113a and 113b is referred to as a Maxwell coil.

Figure 5:
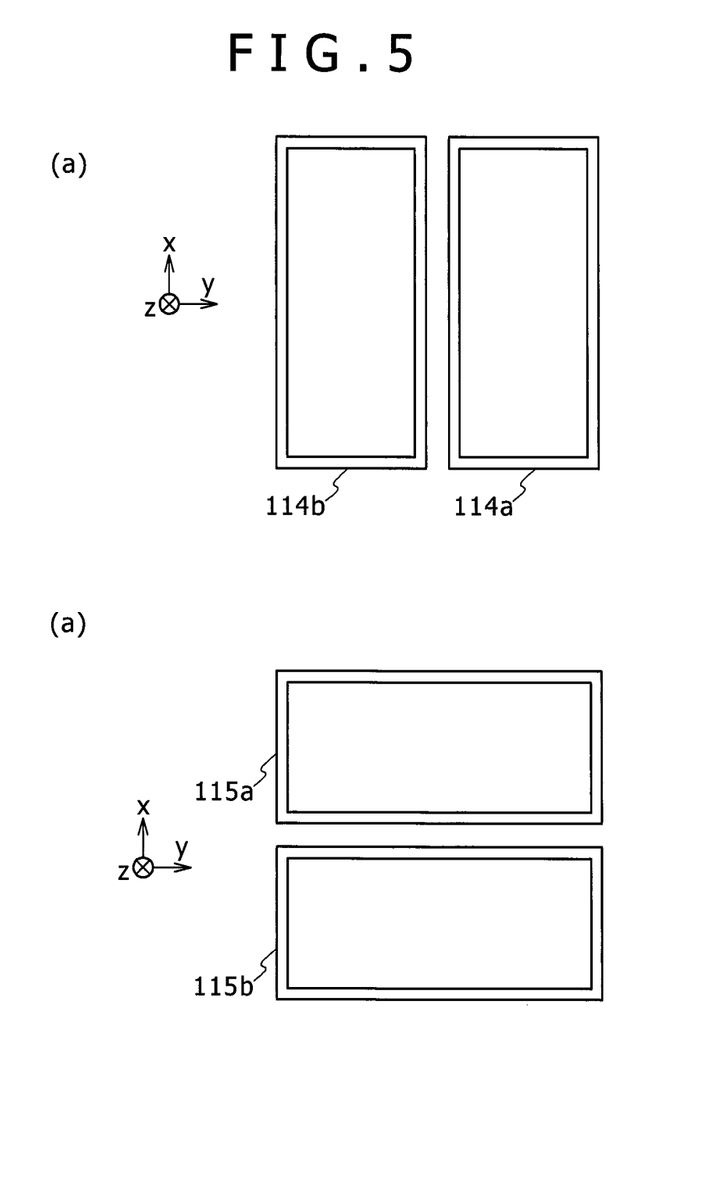
FIG. 5 is a schematic diagram showing a magnetic resonance measuring equipment according to the present embodiment.

Gradient magnetic field coils 114a, 114b, 114c, and 114d are rectangular gradient magnetic field coils that generate a gradient magnetic field $\partial Bz/\partial y$. The gradient magnetic field coils 114a and 114b are disposed side-by-side in the y-direction as shown in FIG. 5(a). In a similar way, the gradient magnetic field coils 114c and 114d are disposed side-by-side in the y-direction. In order to generate a gradient magnetic field ∂Bz/∂y>0, it is necessary to pass currents through a pair of gradient magnetic field coils 114a and 114c that are disposed opposite to each other so that a magnetic field is generated in the +z-direction, and it is also necessary to pass currents through a pair of gradient magnetic field coils 114b and 114d that are disposed opposite to each other so that a magnetic field is generated in the −z-direction. In a similar way, in order to generate a gradient magnetic field ∂Bz/∂y<0, it is necessary to pass all the currents in the directions opposite to those in the case of the gradient magnetic field ∂Bz/∂y>0.

Gradient magnetic field coils 115a, 115b, 115c, and 115d are rectangular gradient magnetic field coils that generate a gradient magnetic field ∂Bz/∂z. The gradient magnetic field coils 115a and 115b are disposed side-by-side in the x-direction as shown in FIG. 5(b). In a similar way, the gradient magnetic field coils 115c and 115d are disposed side-by-side in the x-direction. In order to generate a gradient magnetic field ∂Bz/∂x>0, it is necessary to pass currents through a pair of gradient magnetic field coils 115a and 115c that are disposed opposite to each other so that a magnetic field is generated in the $_+$z-direction, and it is also necessary to pass currents through a pair of gradient magnetic field coils 115b and 115d that are disposed opposite to each other so that a magnetic field is generated in the −z-direction. In a similar way, in order to generate a gradient magnetic field ∂Bz/∂x<0, it is necessary to pass all the currents in the directions opposite to those in the case of the gradient magnetic field ∂Bz/∂x>0.

It becomes possible to generate a static magnetic field with a spatially-known distribution by using gradient magnetic field coils. As described above, because the frequency of a nuclear magnetic resonance signal is proportional to the intensity of the static magnetic field, it becomes possible to interpret information about the frequency and phase of the nuclear magnetic resonance signal as the spatial position of the signal source. In addition, by appropriately handling the gradient magnetic field coils, the behavior of a nuclear spin in the object can be controlled. For example, the gradient-echo method that inverts a gradient magnetic field makes it possible to align the phases of nuclear spins of the nuclear magnetic resonance signal, and to generate the echo signal of the FID signal.

Figure 6:
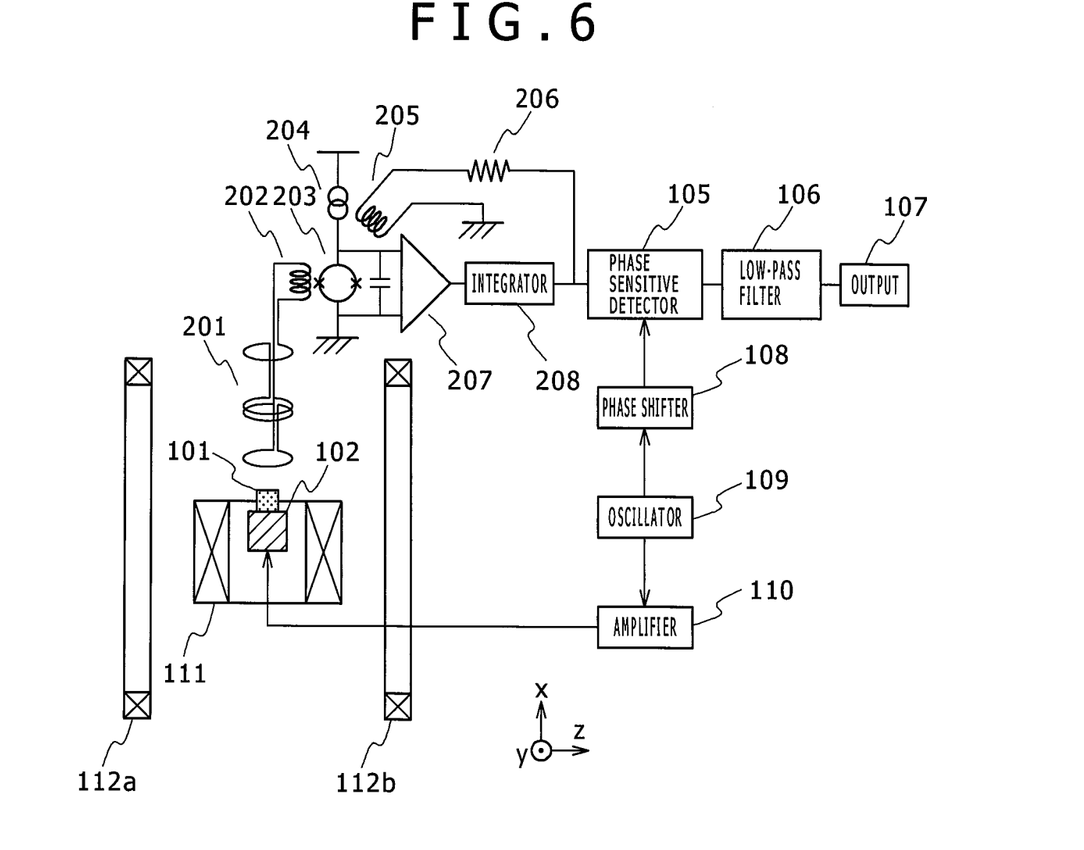
FIG. 6 is a schematic diagram showing a magnetic resonance measuring equipment according to the present embodiment.

FIG. 6 is a schematic diagram showing a magnetic resonance measuring equipment according to the present embodiment. The configuration of the magnetic resonance measuring equipment shown in FIG. 6 is a configuration of the magnetic resonance measuring equipment shown in FIG. 1 to which a SQUID magnetic flux meter is added as a probe for detecting nuclear magnetic resonance signals instead of the detection coil 103 which is an induction coil.

Here, a detection coil 201 detects a nuclear magnetic resonance signal generated from the examination object 101 as a magnetic flux signal that crosses the detection coil 201, and transmits the nuclear magnetic resonance signal to a SQUID 203 via an input coil 202.

A bias current is applied to the SQUID 203 by a current source 204. In this case, a voltage generated between the terminals of the SQUID 203 varies with a cycle of the magnetic flux quantum $\Phi_0$ (=2.07×10$^{-15}$ Wb) owing to a magnetic flux passing through the SQUID 203. After the voltage between the terminals of the SQUID 203 is amplified by an amplifier 207 and integrated by an integrator 208, the voltage is fed back to the SQUID 203 via a feedback coil 205, with the result that the magnetic flux passing through the SQUID 203 is kept constant. The magnetic flux that is fed back to the SQUID 203 is detected as a current flowing through the feedback coil 205, that is, as a voltage generated between the terminals of a feedback resistor 206. This series of SQUID control circuits is referred to as an FLL (flux-locked loop) circuit.

In FIG. 6, as is the case with FIG. 1, the vibration (sonic wave) of the frequency F larger than $f_o$ is applied to the examination object 101 by the vibrator 102, and the examination object 101 is vibrated at the frequency F. At this time, a flux that crosses the detection coil 201 is modulated by the frequency F. The magnetic flux signal detected by the detection coil 201 is transmitted to the SQUID 203 via the input coil 203 as described above, and the transmitted magnetic flux signal is converted into a voltage signal. As described above, being converted from the magnetic flux signal into the voltage signal, the nuclear magnetic resonance signal of the frequency $f_o$ modulated by the frequency F is input into the phase sensitive detector 105. The phase sensitive detector 105 outputs the product of the nuclear magnetic resonance signal of the frequency $f_o$ modulated by the frequency F and the reference signal of the frequency F, and after the product passes through the low-pass filter 106, only the original nuclear magnetic resonance signal can be detected with a high S/N ratio.

The detection coil 201 is a coaxial second derivative type coil, and it is formed by winding superconductive wires such as niobium titanium (NbTi) wires around a bobbin. A derivative type detection coil has an advantage in that the derivative type detection coil can cancel comparatively uniform noise residing in an environmental magnetic field by detecting the spatial gradient of the magnetic field, and it is referred to as a gradiometer. In the above description, although the coaxial second derivative type coil is used, a coaxial first derivative type coil, a planar first derivative type coil, or a two-dimensional gradiometer type coil can be used as the detection coil 201. In addition, in the case where the magnetic resonance measuring equipment is used under a little influence of an environmental magnetic field, a magnetometer that is used for measuring not the spatial gradient of a magnetic field but for measuring the magnetic field itself can be used. Patent Literature 1 discloses the explanation about the above derivative type detection coil.

In addition, the detection coil 201, the input coil 203, and the SQUID 203 are refrigerated under the superconducting transition temperature or lower with a cryogen such as liquid helium or liquid nitrogen, or in a refrigerating machine because the detection coil 201, the input coil 203, and the SQUID 203 are operated in their superconducting state.

Figure 7:
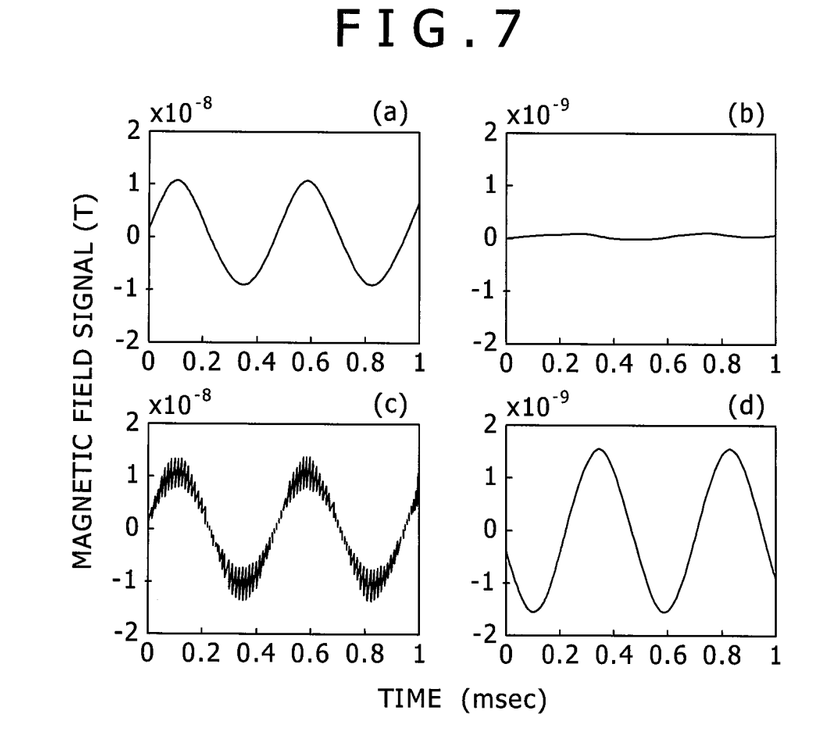
FIG. 7 is a schematic diagram showing measurement signals of the magnetic resonance measuring equipment according to the present embodiment.

FIG. 7 is a schematic diagram showing measurement signals of the magnetic resonance measuring equipment according to the present embodiment. FIG. 7(a) is a diagram showing a magnetic field signal obtained when the nuclear magnetic resonance signal of a proton in the static magnetic field with its intensity 50 μT is detected by the SQUID magnetic flux meter in the case of the examination object 101 being in resting state. As described above, the frequency of the magnetic field signal is 2.1 kHz. On the other hand, FIG. 7(c) is a diagram showing a magnetic field signal obtained when the examination object 101 is vibrated with the vibration frequency 100 kHz. In addition, FIG. 7(d) is a diagram showing a waveform obtained by performing lock-in detection on the signal shown in FIG. 7(c) using a reference signal of the frequency F. On the other hand, FIG. 7(b) is a diagram showing a signal obtained by performing lock-in detection on the unmodulated signal shown in FIG.

7(a) using a reference signal of the frequency F in a similar way as above. It is obvious that the amplitude of the signal is almost vanished. Judging from the above, it is understood that only the nuclear magnetic resonance signal that is derived from the sample and modulated by the vibration frequency F can be measured by this measurement method which employs the modulation using the vibration and the lock-in detection.

Figure 8:
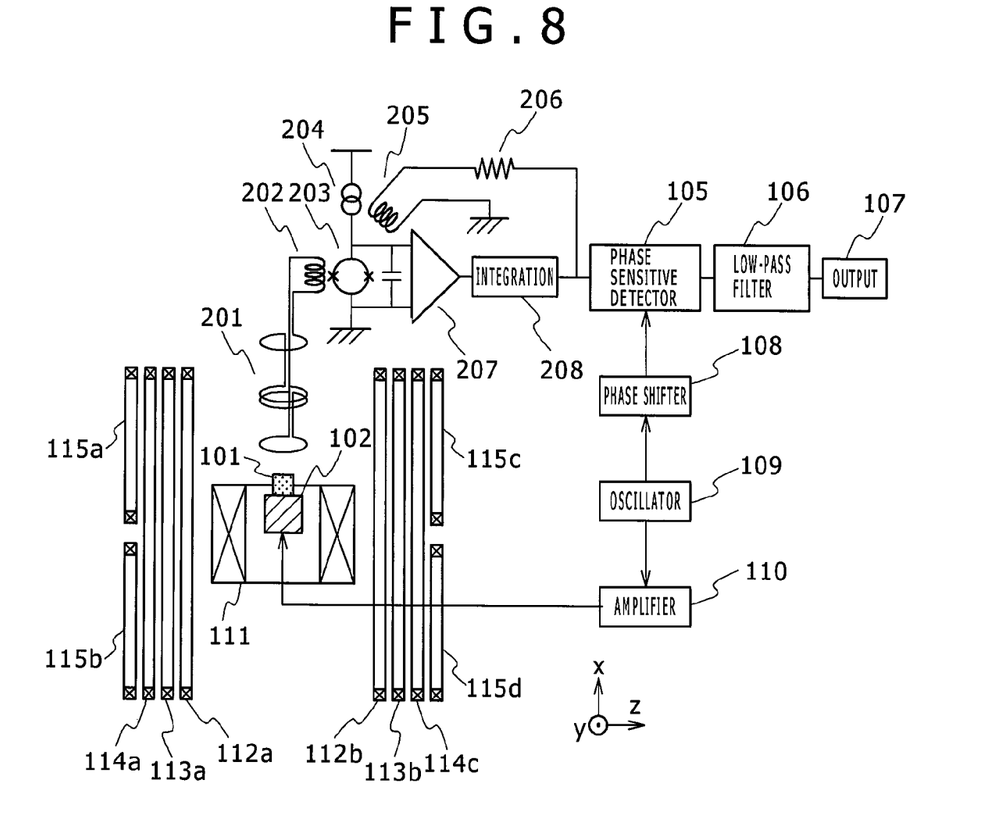
FIG. 8 is a schematic diagram showing a magnetic resonance measuring equipment according to the present embodiment.

FIG. 8 is a schematic diagram showing a magnetic resonance measuring equipment according to the present embodiment. The configuration of the magnetic resonance measuring equipment shown in FIG. 8 is a configuration of the magnetic resonance measuring equipment shown in FIG. 6 to which gradient magnetic field coils are added, with the result that the magnetic resonance measuring equipment shown in FIG. 8 becomes capable of MRI. The configuration of the gradient magnetic field and the detail of MRI are similar to those described in FIG. 4. While the detection coil 103 that is an induction coil is used for detecting the nuclear magnetic resonance signal in FIG. 4, the derivative type detection coil 201, the input coil 202, and the SQUID 203 are used in FIG. 8.

Figure 9:
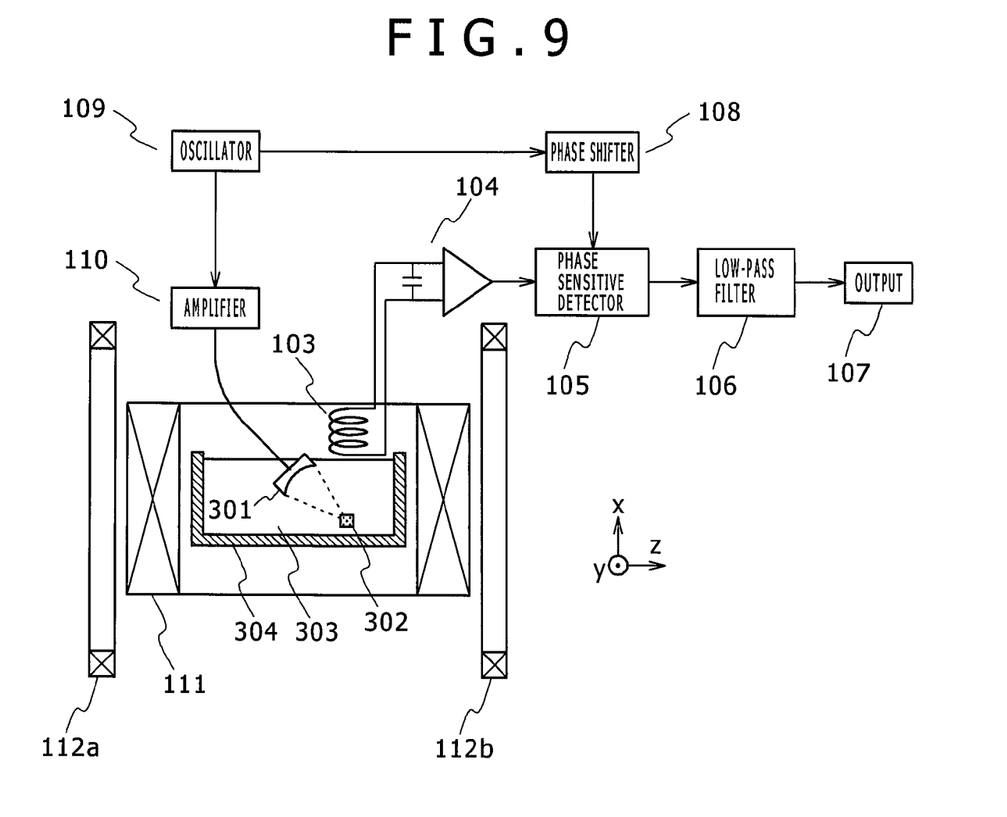
FIG. 9 is a schematic diagram showing a magnetic resonance measuring equipment according to the present embodiment.

FIG. 9 is a schematic diagram showing a magnetic resonance measuring equipment according to the present embodiment. The configuration of the magnetic resonance measuring equipment shown in FIG. 9 is a configuration of the magnetic resonance measuring equipment shown in FIG. 1 in which a converging ultrasonic wave transducer 301 is used instead of the vibrator 102. The converging ultrasonic wave transducer 301 is capable of convergently irradiating a specific small area 302 to be a focus of a converging ultrasonic wave with the ultrasonic wave, and selectively vibrating the specific small area 302.

To put it concretely, only the small area 302 of approximately 1 mm square can be vibrated by the frequency F with the use of the converging ultrasonic wave. The detection method for detecting the modulated nuclear magnetic resonance signal is similar to that described in FIG. 4. However, in this case, the signal that is detected is a signal derived only from the small area 302.

The alignment of the small area is determined by the relation between the converging ultrasonic wave transducer 301 and a focus. In other words, the positional relation between the small area 302 of the examination object and the converging ultrasonic wave transducer 301 is determined by the figuration of the converging ultrasonic wave transducer. Therefore, the alignment of the small area 302 is carried out by moving a vessel 304 containing the examination object 303, or by moving the converging ultrasonic wave probe 301.

The alignment of the small area 302 is performed, while the position of the small area 302 is being monitored with the use of an ultrasonic image measurement device, an X-ray image measurement device, an optical microscope, a camera, or the like in accordance with the examination object 303 that is a target of the examination and the needed resolution.

In addition, it is also desirable that, in order to get high signal sensitivity, the detection coil 103 or the examination object 303 should be moved so that the distance between the detection coil 103 and the small area 302 becomes the shortest. In addition, by scanning plural small areas 302 all over the examination object 303, nuclear magnetic resonance signals regarding the plural small areas 302 are obtained, which makes it possible to detect the nuclear magnetic resonance signals of the examination object 303 with a high resolution. With the use of this method, the spatial distribution of the nuclear magnetic resonance signals can be obtained with a high resolution without using a gradient magnetic field.

Figure 10:
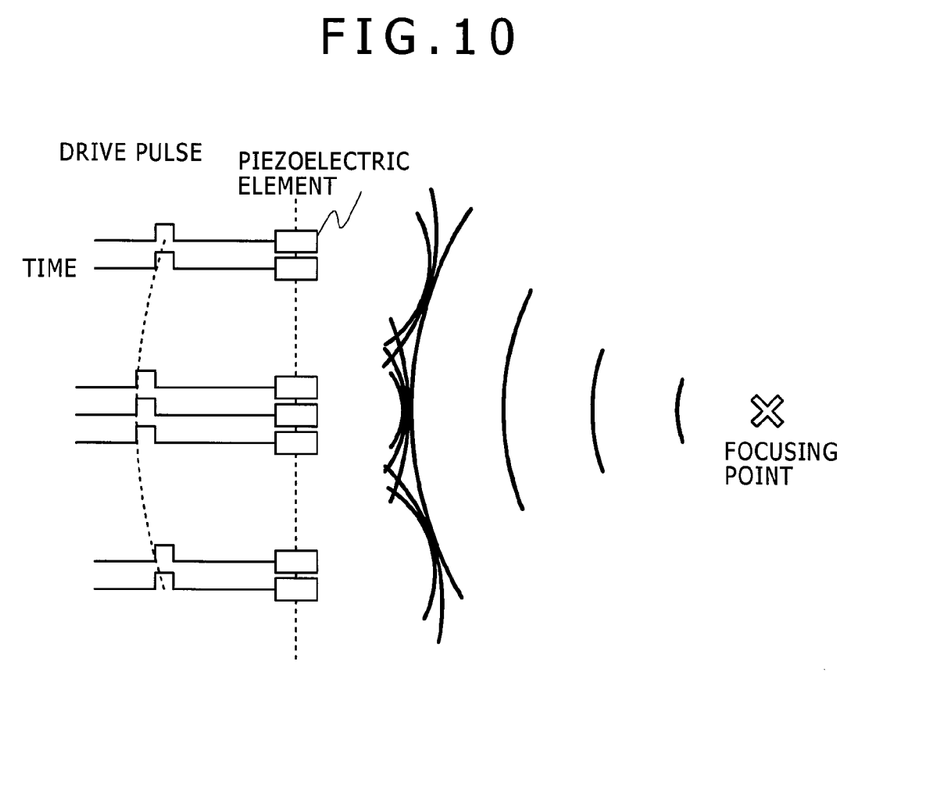
FIG. 10 is a diagram showing an example of electric control over the focus position of a converging ultrasonic wave.
Figure 11:
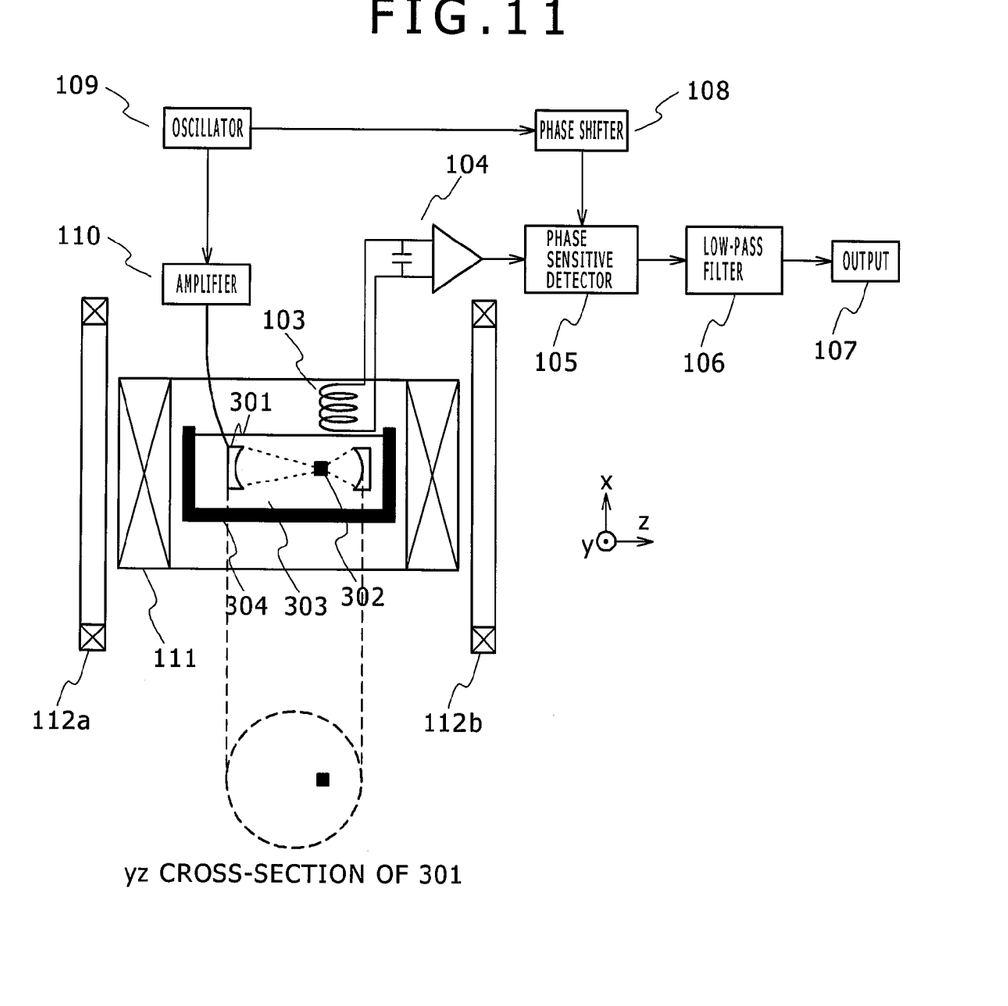
FIG. 11 is a schematic diagram showing a magnetic resonance measuring equipment according to the present embodiment.

FIG. 11 is a schematic diagram showing a magnetic resonance measuring equipment according to the present embodiment. Different from the previous embodiment, the focus position of a converging ultrasonic wave is electrically controlled in this embodiment. The method of the electric control will be explained with reference to FIG. 10. In this electric control, a piezoelectric substance is comprised of plural piezoelectric elements. The distances between respective piezoelectric elements and a convergent point is calculated, and differences among the distances are converted into propagation time differences by dividing the differences among the distances by the speed of sound. By shifting the drive times for respective piezoelectric elements in accordance with these propagation time differences, the ultrasonic wave can be focused on an arbitrary position which is different from the geometric focus point determined by the figuration of the converging ultrasonic wave transducer. With the use of this electric control and a circular transducer surrounding the examination object, it becomes possible that the ultrasonic wave is converged on an arbitrary position of the examination object and that the spatial distribution of vibration amplitudes is controlled.

LIST OF REFERENCE SIGNS

101: examination object
102: piezoelectric substance
103: detection coil
104: tuning amplifier
105: phase sensitive detector
106: low-pass filter
107: output
108: phase shifter
109: oscillator
110: amplifier
111: polarized magnetic field generation coil
112a, 112b: static magnetic field generation coil
113a, 113b: gradient magnetic field generation coil
114a, 114b: gradient magnetic field generation coil
115a, 115b, 115c, 115d: gradient magnetic field generation coil
201: derivative type detection coil
202: input coil
203: SQUID
204: current source
205: feedback coil
206: feedback resistor
207: tuning amplifier
208: integrator
301: converging ultrasonic wave transducer
302: small area of an examination object
303: examination object
304: vessel

The invention claimed is:

1. A magnetic resonance measuring equipment comprising:
a static magnetic field coil which generates a static magnetic field;
a vibrator which applies a vibration to an examination object, the frequency of the vibration being higher than the frequency of a nuclear magnetic resonance signal generated from the examination object;
a lock-in amplifier which performs lock-in detection using the frequency of the vibration as a reference signal; and a probe which detects the nuclear magnetic resonance signal generated from the examination object, wherein the nuclear magnetic resonance signal is modulated by the vibrator, and the modulated nuclear magnetic resonance signal is detected by the lock-in detection.

2. The magnetic resonance measuring equipment according to claim 1, wherein the vibrator is a piezoelectric substance.

3. The magnetic resonance measuring equipment according to claim 1, wherein the vibrator is a speaker.

4. The magnetic resonance measuring equipment according to claim 1, wherein the vibrator is a motor.

5. The magnetic resonance measuring equipment according to claim 1, wherein the probe is an induction coil.

6. The magnetic resonance measuring equipment according to claim 1, wherein the probe is a superconducting quantum interference device (SQUID) magnetic flux meter.

7. The magnetic resonance measuring equipment according to claim 1, wherein the vibrator is a converging ultrasonic wave transducer that generates a converging ultrasonic wave, and a spatial distribution of the nuclear magnetic resonance signal is detected through selectively vibrating a local area of the examination object by the converging ultrasonic wave transducer.

8. The magnetic resonance measuring equipment according to claim 1, wherein an intensity of the static magnetic field is 1 mT (millitesla) or less.

9. A magnetic resonance measuring equipment comprising:
- a static magnetic field coil which generates a static magnetic field;
- a gradient magnetic field coil which generates a gradient magnetic field;
- an RF coil which generates an RF magnetic field;
- a vibrator which applies a vibration to an examination object, the frequency of the vibration being higher than the frequency of a nuclear magnetic resonance signal generated from the examination object;
- a probe to detect the nuclear magnetic resonance signal generated from the examination object; and
- a lock-in amplifier which performs lock-in detection using the frequency of the vibration as a reference signal, wherein the nuclear magnetic resonance signal is modulated by the piezoelectric substance, the nuclear magnetic resonance signal is detected by performing the lock-in detection on the modulated nuclear magnetic resonance signal, and the image of the examination object is depicted.

\* \* \* \* \*